United States Patent [19]

Tustin et al.

[11] Patent Number: 4,778,939

[45] Date of Patent: Oct. 18, 1988

[54] LOW TEMPERATURE OXYIODINATION OF AROMATIC COMPOUNDS

[75] Inventors: Gerald C. Tustin; Mark Rule, both of Kingsport, Tenn.

[73] Assignee: Eastman Kodak Company, Rochester, N.Y.

[21] Appl. No.: 29,896

[22] Filed: Mar. 25, 1987

[51] Int. Cl.$^4$ .............................................. C07C 17/15
[52] U.S. Cl. ...................... 570/203; 570/206; 570/208
[58] Field of Search ................ 570/206, 211, 203, 208

[56] References Cited

U.S. PATENT DOCUMENTS

| | | | |
|---|---|---|---|
| 3,214,482 | 10/1965 | Caropreso et al. | 570/206 |
| 3,363,010 | 1/1968 | Schwarzenbek | 570/203 |
| 3,544,542 | 2/1972 | Prahl et al. | 570/203 |
| 3,600,331 | 8/1971 | Ingwalson | 570/203 |
| 4,240,987 | 12/1980 | Martin et al. | 570/206 |
| 4,391,785 | 7/1983 | Rosinski et al. | 502/77 |
| 4,513,092 | 4/1985 | Chu et al. | 502/77 |

FOREIGN PATENT DOCUMENTS

| | | | |
|---|---|---|---|
| 0181790 | 5/1986 | European Pat. Off. | 570/206 |
| 77631 | 5/1982 | Japan | 570/206 |
| 159496 | 12/1963 | U.S.S.R. | 570/206 |

OTHER PUBLICATIONS

Groggins, "Unit Processes in Organic Chemistry" (1958) Fifth Ed, McGraw-Hill Book Co., Inc., p. 262.
Advanced Organic Chemistry: Reactions, Mechanisms, and Structure, March, McGraw-Hill, 1968, p. 405.
J. Org. Chem., vol. 35, No. 10, 1970, Baird et al, Halogenation with Copper(II) Halides. The Synthesis of Aryl Iodides.
Institute of Catalysis, Siberian Branch of the Academy of Sciences of the USSR, vol. 23, No. 4, pp. 992–994, Jul.-Aug., 1982; Gorodetskaya et al, Oxidative Bromination of Aromatic Compounds.
Chemical Economy & Engineering Review, Apr. 1984, vol. 16, No. 4, (No. 177) Itatani: International Technological Trends in $C_1$ Chemistry.

*Primary Examiner*—Werren B. Lone
*Attorney, Agent, or Firm*—Charles R. Martin; William P. Heath, Jr.

[57] ABSTRACT

The invention relates to a process for iodinating an aromatic compound which comprises reacting iodine and the aromatic compound over a non-acid catalyst, wherein the catalyst has been contacted with an alkali or alkaline earth metal salt, with a source of iodine and a source of molecular oxygen.

14 Claims, No Drawings

LOW TEMPERATURE OXYIODINATION OF AROMATIC COMPOUNDS

BACKGROUND OF THE INVENTION

1. Field of the Invention

The present invention relates to processes for iodinating aromatic compounds over non-acid catalysts impregnated with alkali or alkaline earth salts wherein the catalysts have enhanced activity at low temperatures.

2. Background of the Invention

It has long been desired to be able to derivatize aromatic compounds and in particular condensed ring aromatic compounds in commercially attractive quantities since many of these compounds possess properties which would fill long sought needs. In particular, the compound 2,6-naphthalene dicarboxylic acid or its esters is particularly desired for use in the manufacture of polyesters which would have excellent barrier properties when fabricated into films, bottles or coatings. However, known techniques for producing 2,6-naphthalene dicarboxylic acid and esters are very expensive and impractical for commercial exploitation.

3. Description of the Prior Art

Synthesis of iodobenzene starting from benzene and iodine is usually carried out in the liquid phase in the presence of an oxidative agent, preferably nitric acid. Such techniques have been described in the literature and in particular in Japanese No. 58/77830, U.S.S.R. Patent No. 453392 and by Datta and Chatterjee in the *Journal of the American Chemical Society*, 39 437, (1917). Other oxidative agents have also been suggested but none of these have proven to be more efficient or convenient than nitric acid. typical of the other oxidative agents which have been suggested are iodic acid, sulfur trioxide and hydrogen peroxide as described by Butler in the *Journal of Chemical Education*, 38, 508, (1971). The use of metal halogenides to catalyze iodination has been suggested by Uemura, Noe, and Okano in the *Bulletin of Chemical Society of Japan*, 47, 147, (1974). The concept of direct iodination of benzene in the gas phase over the zeolite 13X has been suggested by Japanese Patent Publication 82/77631 in the absence of any oxidizing agent.

Ishida and Chono in Japanese *Kokai* 59/219241 have suggested a technique for oxyiodinating benzene over very acidic zeolite catalyst having a silica to alumina ($SiO_2$:$Al_2O_3$) ratio of greater than 10. In this technique benzene is reacted with iodine in the presence of oxygen to produce iodinated benzene. According to this disclosure approximately 96% of the benzene which is converted to iodinated form. However, the remaining benzene is oxidized to carbon dioxide and other combustion products resulting in the loss of valuable starting material.

Paparatto and Saetti disclosed in European Patent Application Nos. 181,790 and 183,579 techniques for oxyiodination of benzene over zeolite catalysts. European Patent Application No. 181,790 suggests the use of ZSM-5 and ZSM-11 type zeolites which has been exchanged prior to use with the least one bivalent or trivalent cation. According to this disclosure the utilization of these zeolites in the acid or alkaline form results in a rapid decrease in catalytic activity in relatively few hours.

European Patent Application No. 183,579 suggests the utilization of X type or Y type of zeolite in non-acid form. According to 183,579 the X or Y zeolites have to be used in the form exchanged with mono-valent, bivalent or trivalent cations and in particular with alkaline or rare earth cations. The techniques of 181,790 and 183,579 prepare the mono-iodobenzene in selectivities in excess of 90% and only distinctly minor amounts of the diiodobenzene compounds.

Accordingly, a need exists for a process which can iodinate benzene at high conversions with substantially no oxidation of the benzene ring.

Further need exists for a process which selectively produces para-diiodobenzene with substantially no oxidation of the benzene ring.

Another need exists for a process which iodinates naphthalene preferentially at the 2-position with minimum formation of oxidation products.

A further need exists for a process which selectively produces 2,6-diiodonaphthalene with minimal oxidation of the naphthalene starting material.

Still a further need exists for a process which selectively produces 2,6-diiodonaphthalene or p-diiodobenzene with minimal oxidation of the starting materials and decreased formation of triiodoaromatics.

RELATED APPLICATIONS

Copending Application Nos. 912,806, filed Sept. 29, 1986; Ser. No. 029,959 filed Mar. 25, 1987; and Ser. No. 029,898 filed Mar. 25, 1987 disclose techniques for iodinating aromatic compounds over non-acidic catalysts. The selectivities of these techniques to the desired products is improved by conducting the techniques at comparatively low temperatures on the order of about 100°C.–250° C. However, the activity of the catalyst is substantially reduced at these low temperatures as compared to the activity obtained at higher temperatures, i.e., greater than about 250° C.

Copending application Ser. nos. 029,899 filed Mar. 25, 1987; Ser. No. 029,956 filed Mar. 25, 1987; and Ser. No. 029,949 filed Mar. 25, 1987 disclose transiodination-/isomerization reactions which may be used in conjunction with an oxyiodination reaction.

Copending application Ser. No. 029,887 filed Mar. 26, 1987 is directed to a method of iodinating substituted aromatic compounds.

The disclosures of the above-identified patent applications are incorporated herein by reference.

SUMMARY OF THE INVENTION

One object of the present invention is to provide a technique for increasing the low-temperature catalytic activity of zeolite catalysts utilized in the iodination of benzene.

Yet another object comprises a process for the selective low-temperature iodination of benzene to para-diiodobenzene over a zeolite catalyst at high catalytic activity.

Yet a further object of the present invention comprises the technique of low-temperature iodination of naphthalene in the 2-position over a zeolite catalyst at high catalytic activity.

A further object of the present invention comprises a process for the selective low-temperature iodination of naphthalene to 2,6-diiodonaphthalene over a zeolite catalyst at high activity.

These and further objects of the present invention which will become apparent from the following disclosure have been attained by a process which comprises reacting an aromatic compound over a non-acid zeolite catalyst, wherein said catalyst has been impregnated with alkali or alkaline earth salts, with a source of iodine and a source of molecular oxygen.

DESCRIPTION OF THE PREFERRED EMBODIMENTS

The aromatic compounds which can be utilized in practice of the present invention are essentially any aromatic compound including substituted and unsubstituted aromatics. Suitable aromatic compounds include hydrocarbon aromatics, nitrogen containing aromatics and sulfur containing aromatics. Typical hydrocarbon aromatics include benzene and biphenyl, condensed ring aromatics such as naphthalene and anthracene, sulfur containing aromatics including thiophene and benzothiophene, nitrogen containing aromatics such as pyridine and benzopyridine, and substituted aromatics such as sulfones, diaryl ethers, diaryl carbonyls, diaryl sulfides and the like. Aromatic compounds substituted by alkyl groups are generally not preferred for utilization in the present technique. It has been found that alkyl substituted aromatics the iodination reaction is not limited to the aromatic ring but that one obtains a mixture of products. That is, the products are iodinated not only on the ring but also on the side chains. Thus, while alkyl substituted aromatics can be utilized in the present technique their use is not preferred.

The catalyst which may be employed in the present technique are described in copending applications Ser. Nos. 912,806, filed Sept. 29, 1986 and Ser. No. 029,959 filed Mar. 25, 1987. The disclosure of these applications are incorporated herein by reference for a more complete description of the catalyst and reaction conditions which are to be employed.

The catalysts utilized in the present technique are generally characterized as zeolite containing non-acid sites, and more preferably basic sites. The most preferred catalyst for use in the present invention are zeolites in the non-acid form.

The type of zeolite which is utilized is not critical so long as greater than 10% of the exchangeable cations are alkali, alkaline earth or rare earth metals and the pore size is greater than about 6 Å. Since benzene as well as naphthalene have apparent ring sizes of about 6 Å this is the lower limit on the pore size of the zeolite catalyst which is useful. If the aromatic compound cannot enter into the pore on the zeolite catalyst then only very little conversion of the aromatic compounds will occur. Further, if the zeolite is in the acid form, excessive combustion or oxidation of the aromatic compound will occur which is not preferred. Hence, the preferred zeolites are all in the non-acid form and all contain a pore size of about 6 Å or larger.

In general, the reaction rate is a function of silicon to aluminum ratio in the zeolite, since aluminum is part of the active site. It is preferred to use zeolites with a silicon (as Si) to aluminum (as Al) ratio of 10:1 or less, more particularly 5:1 or less. Still more preferred are those zeolites having a silicon to aluminum ratio of 3:1 or less with the most preferred type having a silicon to aluminum ratio of 1.5 or less. Particular types of zeolites which have proven to be particularly effective are the X and Y types. The Y type zeolite generally has a silicon to aluminum ratio of about 1.5 to 1 to 3:1. The X type zeolite is generally considered to have a silicon to aluminum ratio of 1:1 to 1.5:1. The X type zeolite exhibits more sensitivity to the counter ion than the Y type does. That is, the selectively of this X type zeolite to the production of specific mono, di or tri iodinated aromatic compounds can be altered more successfully with the selection of the appropriate counter ions than can the Y type. While not being bound to any particular theory, it is believed that the counter ion affects the selectivity by altering the shape of the pore thereby increasing or decreasing the selectivity of the catalyst for any particular isomer as compared with the standard sodium form. As the number of cations at the active site decreases the degree of change possible in the shape of the pore decreases and thus selectivity control decreases. Thus, when one desires to produce a particular isomer high alumina content zeolites are preferred. The most preferred zeolite to produce 2,6-diiodonaphthalene is the 13 X type where a significant fraction of the exchangeable cations are potassium, rubidium or cesium. The ratio of 2,6- to 2,7-diiodonaphthalene generally increases with increasing amounts of these ions.

We have found that the selectivity of these zeolite catalysts toward p-diiodobenzene, 4,4′-diiodobiphenyl or 2,6-diiodonaphthalene is substantially improved by operating at the comparatively low temperatures of about 200° C. Similar temperature ranges would be used for other aromatic compounds. However, at these lower temperatures catalyst activity is greatly reduced.

We have found that we can increase the activity of these catalysts at low temperatures by impregnating the catalyst with alkali or alkaline earth salts. The salt-treated catalysts possess enhanced oxyiodination activity at low temperatures, and in addition possess increased selectivity compared to the untreated catalyst at the same reaction temperature.

The preferred salts are inorganic salts of alkali or alkaline-earth metals. Particularly preferred cations are potassium, rubidium and cesium cations. The anion utilized in the inorganic salt is not critical. Anions such as bromide, chloride, nitrate, fluoride, iodide, sulfate, vanadate, carbonate, hydroxide and the like have proven effective. While not critical, the preferred anions are chloride, bromide, iodide and sulfate. Particularly preferred anions are the halides. Under oxyiodination conditions the anion may eventually be replaced by iodide.

The amount of salt which may be impregnated into the catalyst is dependent on the alumina content of the zeolite. For the X-type zeolites, as much as 0.2 moles of salt per 100 grams of zeolite can be absorbed. With potassium iodide as the salt, this corresponds to 30 grams KI per 100 grams of zeolite. Of course, lesser or greater amounts of salt may be utilized depending on the type of zeolite. Preferably, the amount of salt utilized is 0.001 to 0.1 mole per 100 grams of catalyst, more preferably 0.01 to 0.05 mole per 100 grams of catalyst.

The catalyst may be impregnated with the alkali or alkaline-earth metal salt by any suitable technique. A preferred technique is to add the catalyst to an aqueous solution containing a known amount of the desired salt and evaporating the water. The resulting impregnated catalyst may be used as is or may be calcined prior to use. The temperature and length of the calcining process is dependent on the particular catalyst used.

While not being bound to any particular theory, it is believed that the inorganic salts in the ionized form are "dissolved" in the catalyst, particularly the zeolite catalyst such as the X and Y types, which possess strong electrostatic fields within the zeolite cavity. Relatively few of the cations in the zeolite possess particularly strong fields; these are the active sites. Dissolving these salts in the zeolite increase the local electrostatic field strength the number of active sites. Catalysts which are salt-treated as noted above possess enhanced oxyiodination activity at low temperatures, and in addition possess increased selectivity compared to the untreated zeolite at the same reaction temperature.

The temperature at which the reaction is conducted is not critical and can be any temperature at which the aromatic compound is fluid. The maximum temperature at which the process can be carried out is that at which combustion of the aromatic compound occurs. Generally, temperatures of from about 100° to 500° C. have been found satisfactory, with temperatures of from about 200° to 400° being preferred, more preferably from about 200° to 250° F. When operating at the lower ranges, the inorganic salts have their greatest effect in increasing the activity of the iodination catalyst.

The pressure which the process is conducted is not critical and can range from subatmospheric to superatmosphric. The utilization of elevated pressures in the gas phase process may be preferred so as to minimize equipment size. In general, pressures form atmospheric to 600 psig have proven satisfactory although higher or lower pressures can be utilized. The reaction may also be carried out in the liquid phase.

The molecular oxygen can be introduced as pure oxygen, air or oxygen diluted with any other inert material such as carbon dioxide or water vapor. Essentially oxygen from any convenient source may be utilized. The purpose of the oxygen is to regenerate the active site on the catalyst to its active form once the iodination reaction has occurred. Thus, the amount of oxygen present during the reaction is not critical. However, it is preferred that at least ½ mole of oxygen be used for every mole of iodine. The molar ratio of iodine to aromatic which is to be reacted is not critical and is largely determined by whether one desires to produce a monoiodinated aromatic product or polyiodinated aromatic product. Stroichiometrically, ½ mole of iodine reacts with 1 mole of aromatic compound to produce the monoiodinated form. Similarly, 1 mole of iodine is required to convert 1 mole of aromatic compound to the diiodinated form. Greater or lesser quantities of iodine can be utilized as the artisan may desire. In general, it is desired to run the process to obtain as close to 100% conversion of the iodine as practical so as to simplify the purification steps in the recovery of any unreacted iodine. Suggested mole ratios of aromatic to iodine to oxygen are from 1:0.5:.25 to about 1:2:3. However, other ratios may be utilized as desired.

Essentially any source of iodine may be employed including elemental iodine, $I_2$, hydriodic acid in gaseous form, or alkyl iodides, preferably lower alkyl iodides. Furthermore, mixtures of these materials may be used as the source of iodine.

It is anticipated by the present process would be carried out continuously by the continuous addition of iodine, oxygen and aromatic compound to the reactor, however, the process can be carried out on a batch or semi-batch process as desired. Further, the aromatic compound and iodine can be reacted over the catalyst to produce the iodinated product, the addition of the aromatic compound and iodine then being terminated and oxygen then added to the reactor to regenerate the catalyst to its active form and then the process commenced again. Alternatively, in a continuous process it is possible to utilize two reactants circulating the catalyst between them. In the first reactor the iodine and aromatic compound would be added and reacted to form the iodinated compound. The catalyst would then be circulated to the second reactor where it would be contacted with oxygen to be regenerated and then recycled to the first reactor to catalyze additional reactions of aromatic compound with iodine.

Additionally, the low temperature oxyiodination process may be coupled with any of the transiodination processes disclosed in U.S. application Ser. No. 029,899, Ser. No. 029,956, and Ser. No. 029,949 noted above. In the coupled processes, the iodinated product of the oxyiodination reaction is fed to a selective or non-selective transiodination catalyst or is fed to both types of transiodination catalysts sequentially. The order of the transiodination catalysts is optional.

The space velocity of the process is not critical and may be readily selected by the artisan. Gas hourly space velocity is between 10 and 50,000, preferably between 100 and 20,000 liters per hour of reagents per liter of active zeolite have proven satisfactory.

The catalyst is proven to have an extremely long life and degrades only slowly with time. The degradation of the catalyst is believed to be caused by the combustion of very small quantities of the aromatic compound which deposits small quantities of carbon on the active sites thereby degrading the catalyst activity. When the reaction conditions are selected such that none of the aromatic starting material is oxidized, the life of the catalyst is essentially indefinite. However, when the catalyst becomes deactivated reactivation is simple. An excellent regeneration technique comprises passing air or oxygen over the catalyst for several hours at elevated temperatures. Typically the temperature is above 400° C. although higher or lower temperatures are proven equally satisfactory. The temperature need only be high enough so as to ensure combustion of the carbon deposit on the catalyst. When pure oxygen is employed lower temperatures can be utilized, while when air is employed temperatures on the order of about 400° C. have proven satisfactory.

The following examples are presented to illustrate the present invention but are not intended in any way to limit the scope of the invention which is defined by the appended claims.

The following examples illustrate the operation of this invention in comparison with the unmodified catalyst. All analyses are mol %. In these examples, 50 ml of catalyst is heated to the desired temperature by a tube furnace and a mixture of naphthalene, iodine, and air is passed over the catalyst at a rate of 3 mmol/min naphthalene, 2.25 mmol/min iodine, and 2.9 mmol/min oxygen.

EXAMPLE 1

50 ml KX (50% exchanged with potassium) 16-40 mesh; 225° C. After 2.6 hours the product distribution was 68.2% naphthalene, 21.0% 2-iodonaphthalene, 9.1% 1-iodonaphthalene, and 1.6% diiodonaphthalenes. Iodine conversion was 22%.

EXAMPLE 2

50 ml KX (same as Example 1 but containing 4 wt % KCl); 225° C. After 2.5 hours the product distribution was 17.4% naphthalene, 33.7% 2-iodonaphthalene, 12.6% 1-iodonaphthalene, and 35.0% diiodonaphthalenes. Iodine conversion was 77%.

EXAMPLE 3

50 ml KX (same as Example 1 but containing 3 wt % sodium sulfate); 225° C. After 2.7 hours the product distribution was 42.3% naphthalene, 23.9% 2-iodonaphthalene, 10.2% 1-iodonaphthalene, and 22.9% diiodonaphthalenes. The iodine conversion was 53%.

EXAMPLE 4

50 ml KX (same as Example 1 but containing 6.4 wt % KCl); 250° C. After 4.1 hours the product distribution was 9.8% naphthalene, 30.5% 2-iodonaphthalene, 10.7% 1-iodonaphthalene, and 47.2% diiodonaphthalenes. The iodine conversion was 90%.

EXAMPLE 5

50 ml KX (same as Example 1 but containing 12.0 wt 5 KBr); 250° C. After 4.3 hours the product distribution was 5.8% naphthalene, 23.2% 2-iodonaphthalene, 8.7% 1-iodonaphthalene, and 53.0% diiodonaphthalenes. The iodine conversion was 90%.

EXAMPLE 6

50 ml KX (comparative example, same catalyst as Example 1); 250° C. After 4.5 hours the product distribution was 38.3% naphthalene, 30.2% 2-iodonaphthalene, 11.7% 1-iodonaphthalene, and 19.6% diiodonaphthalenes. The iodine conversion was 54%. The 2,6/2,7 ratio was 1.6.

EXAMPLE 7

50 ml KX (same catalyst as Example 1 but containing 30 wt % KI); 250° C. After 2.5 hours the product distribution was 38.9% naphthalene, 23.3% 2-iodonaphthalene, 22.3% 1-iodonaphthalene, and 26.5% diiodonaphthalenes. The iodine conversion was 60%. The 2,6/2,7 ratio was 5.0.

The invention has been described in detail with particular reference to preferred embodiments thereof, but it will be understood that variations and modifications will be effected within the spirit and scope of the invention.

We claim:

1. A process for iodinating a hydrocarbon, ring nitrogen-containing or ring sulfurcontaining aromatic compound, said process comprising the steps of:
   (a) contacting a non-acidic zeolite catalyst with an alkali or alkaline earth metal salt and then
   (b) reacting iodine, the hydrocarbon, ring nitrogen-containing, or ring sulfurcontaining aromatic compound, and molecular oxygen in the presence of the non-acid zeolite catalyst at a temperature between 100° and 500° C.

2. The process of claim 1, wherein said non-acid catalyst is a zeolite.

3. The process of claim 2, wherein said zeolite contains about 130 wt % of said alkali or alkaline earth metal salt.

4. The process of claim 3, wherein the cation of said salt is potassium.

5. The process of claim 3, wherein the anion of said salt is selected from the group consisting of bromide, chloride, fluoride, iodide, sulfate, vanadate, carbonate and hydroxide.

6. The process of claim 5, wherein said zeolite is the 13X type and contains potassium, rubidium or cesium counterions.

7. The process of claim 1, wherein the temperature during said reacting step is between 200° and 400° C.

8. The process of claim 7, wherein the temperature during said reacting step is between 200° and 250° C.

9. The process of claim 1, wherein the aromatic compound is benzene.

10. The process of claim 1, wherein the aromatic compound is naphthalene.

11. The process of claim 1, wherein the aromatic compound is biphenyl.

12. The process of claim 1, wherein said iodine is provided by reacting a source of iodine selected from the group consisting of elemental iodine, hydroiodic acid and alkyl iodides.

13. The process of claim 1, wherein said molecular oxygen is reacted as pure oxygen, air or oxygen diluted with an inert material.

14. The process of claim 1, wherein said aromatic compound is selected from the group consisting of benzene, biphenyl, naphthalene, anthracene, thiophene, benzothiophene, pyridene and benzopyridine.

* * * * *